United States Patent [19]

Carrez et al.

[11] Patent Number: 5,783,414
[45] Date of Patent: Jul. 21, 1998

[54] EXPRESSION SYSTEM, INTEGRATION VECTOR AND CELL TRANSFORMED BY THIS INTEGRATION VECTOR

[75] Inventors: Dirk Carrez, Strombeek-Bever; Joël Roos, Frasnes-lez-Auraing, both of Belgium

[73] Assignee: Genencor International, Inc., Rochester, N.Y.

[21] Appl. No.: 379,926

[22] Filed: Jan. 27, 1995

[30] Foreign Application Priority Data

Jan. 28, 1994 [BE] Belgium ............................... 09400102
Jun. 17, 1994 [BE] Belgium ............................... 09400586
Jan. 9, 1995 [BE] Belgium ............................... 09500014

[51] Int. Cl.$^6$ ............................................. C12P 21/02
[52] U.S. Cl. ......................... 435/69.1; 435/190; 435/225; 435/254.3; 435/320.1; 536/23.2; 536/24.1
[58] Field of Search ............................... 435/69.1, 70.1, 435/71.1, 225, 254.3, 320.1, 190; 536/24.1, 23.2; 935/22, 27, 33, 41, 35, 68, 37

[56] References Cited

U.S. PATENT DOCUMENTS

| 5,094,951 | 3/1992 | Rosenberg | 435/190 |
| 5,266,688 | 11/1993 | Rosenberg | 536/23.2 |
| 5,360,732 | 11/1994 | Berka et al. | 435/192 |
| 5,360,901 | 11/1994 | Berka et al. | 536/23.2 |

FOREIGN PATENT DOCUMENTS

| 0 238 023 | 9/1987 | European Pat. Off. . |
| 0 249 350 | 12/1987 | European Pat. Off. . |
| 0292609 | 11/1988 | European Pat. Off. . |
| 0 357 127 | 3/1990 | European Pat. Off. . |
| 0 570 075 | 11/1993 | European Pat. Off. . |
| WO 84/02921 | 8/1984 | WIPO . |
| WO 89/12675 | 12/1989 | WIPO . |
| WO 93/18166 | 9/1993 | WIPO . |

OTHER PUBLICATIONS

Verdoes et al. "The Effect of Multiple Copies of the Upstream Region on Expression of The *Aspergillus niger* Glucoamylase–Encoding Gene" Gene 145 179–187 1994.
Hodgkius et al. "Expression of The Glucose Oxidase Gene from *Aspergillus niger*. . . " Yeast 9 625–635 1993.
De Baetseller et al. Fermentation of a Yeast Producing *A. Niger* Gluclose Oxidase Bio/Technol. 9 559–561 1991.
Applied and Enviromental Microbiology, Apr. 1992, pp. 1190–1194, vol. 58, No. 4, Cor F.B. Witteveen, et al., "Localization of Glucose Oxidase and Catlase Activities in *Aspergillus Niger*".
Curr. Genet., 1990, vol. 18, No. 531, pp. 531–536, H. Whittington, et al., "Expression of the *Aspergillus Niger* Glucose Oxidase Gene in *A. Niger, A. Nidulans* and *Saccharomyces Cerevisiae*".
Analytical Biochemistry, vol. 135, pp. 416–422, 1983, Robert C. Garber, et al., "Isolation of DNA From Filamentous Fungi and Separation into Nuclear, Mitochondrial, Ribosomal, and Plasmid Components".

Notice/kit: "Geneamp DNA Amplification Reagent Kit With Amplitaq Recombinant Taq DNA Polymerase", pp. 1–5.
Science, vol. 239, Jan. 29, 1988, Randall K. Saiki, et al., "Primer–Directed Enzymatic Amplification of DNA with a Thermostable DNA Polymerase", pp. 487–491.
Tetrahedron Letters, vol. 22, No. 20, pp. 1859–1862, 1981, S.L. Beaucage, et al., "Deoxynucleoside Phosphoramidites—A New Class of Key Intermediates for Deoxypolynucleotide Synthesis".
Molecular Cloning—a laboratory manual, T. Maniatis, et al., 1982, pp. 374–379, "Constructing Maps of Sites Cleaved By Restriction Endonucleases".
The Journal of Biological Chemistry, vol. 265, No. 7, Mar. 1990, pp. 3793–3802, Katherine R. Frederick, et al., "Glucose Oxidase From *Aspergillus Niger*".
Molecular Cloning—a laboratory manual—second edition, 1989, J. Sambrook, et al., pp. 1.68–1.69; pp. 5.28–5.32; and pp. 9.52–9.55.
Current Protocols in Molecular Bioogy, F.M. Ausubel, 1989, "Size Fractionation Using Sucrose Gradients", pp. 5.3.2–5.3.8.
J. Mol. Biol., 1983, vol. 166, pp. 557–580, Douglas Hanahan, "Studies on Transformation of *Escherichia Coli* with Plasmids".
Bethesda Research Laboratories, (BRL), 1986, Focus vol. 8, No. 2, p. 9, "Tools for the Molecular Biologist".
The EMBO Journal, vol. 3, No. 5, pp. 1097–1102, 1984, E. Boel, et al., "Glucoamylases G1 And G2 From *Aspergillus Niger* are Synthesized From Two Different But Closely Related mRN As".
Proc. Natl. Acad. Sci. USA, vol. 74, No. 12, pp. 5463–5467, Dec. 1977, F. Sanger, et al., "DNA Sequencing With Chain–terminating Inhibitors".
Notice/kit (BIORAD), "Muta–gene Phagemid In Vitro Mutagenesis Kit", Instruction Manual, pp. 1–26.
Bio/Technology, vol. 3, Nov. 1985, Jingdong Zhu, et al., "A Method for Fast and Pure DNA Elution from Agarose Gels by Centrifungal Filtration", pp. 1012, 1015–1016.
Advances in Genetics, vol. 5, 1953, pp. 141–238, G. Pontecorvo, et al.,"The Genetics of *Aspergillus Nidulans*".
Gene, vol. 94, 1990, pp. 147–154, Dirk Carrez, et al., "Heterologous Gene Expression by Filamentous Fungi: Secretion of Human Interleukin–6 by *Aspergillus Nidulans*".

(List continued on next page.)

*Primary Examiner*—Nancy Degen
*Attorney, Agent, or Firm*—Cooley Godward LLP

[57] ABSTRACT

The invention relates to an expression system which is usable for the extracellular production of glucose oxidase, which comprises the sequence of a promoter, the glucose oxidase secretion signal sequence, the mature glucose oxidase sequence and the sequence of a terminator. The invention also relates to an integration vector containing the expression system, and to a cell transformed by this vector.

28 Claims, 8 Drawing Sheets

OTHER PUBLICATIONS

Molecular and Cellular Biology, Aug. 1983, vol. 3, No. 8, pp. 1430–1439, Michael J. Hynes, et al., "Isolation of Genomic Clones Containing the amdS Gene of *Aspergillus Nidulans* and their use in the Analysis of Structural and Regulatory Mutations".

The EMBO Journal, vol. 4, No. 2, pp. 475–479, 1985, Joan M. Kelly, et al., "Transformation of *Aspergillus Niger* by the amdS Gene of *Aspergillus Nidulans*".

Enzyme Microb. Technol., Dec. 1986, vol. 8, Jan Fiedurek, et al., "Screeing and Mutagenesis of Moulds for the Improvement of Glucose Oxidase Production", pp. 734–736.

Molecular Cloning—a laboratory manual—second edition, J. Sambrook, et al., 1989, pp. 1.25–1.28; 1.63–1.73; 1.75; 6.22–6.35; 9.24.

Molecular Cloning—a laboratory manual—second edition, J. Sambrook, et al., 1989, pp. 13.45–13.58.

Molecular Cloning—a laboratory manual—second edition, 1989, J. Sambrook, et al., pp. 13.14–13.17.

J. Cell. Biol., No. 10, p. 274, Feb. 1986, K. Hayenga, et al., "Expression and Secretion of Bovine Calf Chymosin by *Aspergillus Nidulans*".

Appl. Biochem. Microbiol., vol. 14, No. 3, p. 369, 1978, S.A.Z. Mahmoud, et al., "Isolation and Purification of a Glucoamylase Preparation from a Submerged Culture of Aspergillus Foetidus ATCC 14916".

Applied Microbiology, vol. 25, No. 6, pp. 890–895, Jun. 1973, L. T. Chang, et al., "Intergenic Complementation of Glycoamylase and Citric Acid Production in Two Species of Aspergillus".

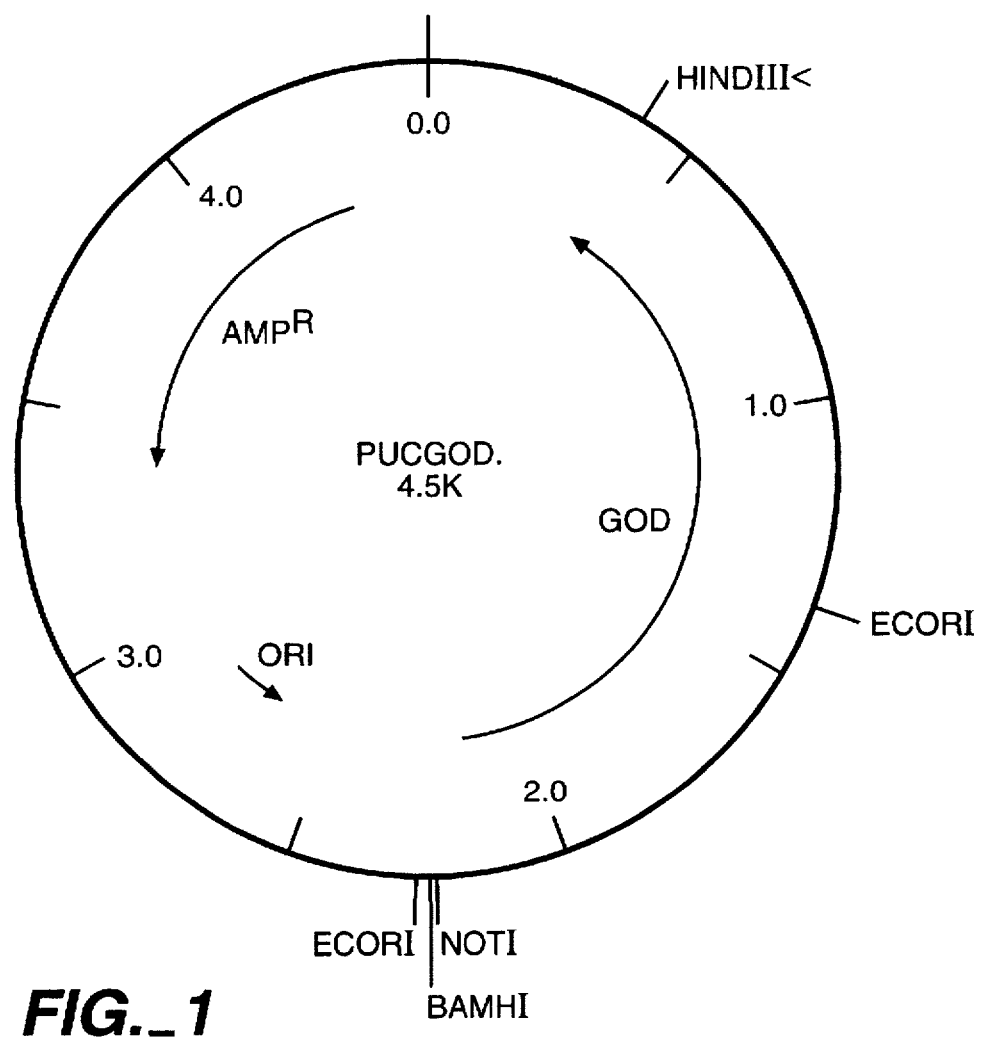
FIG._1

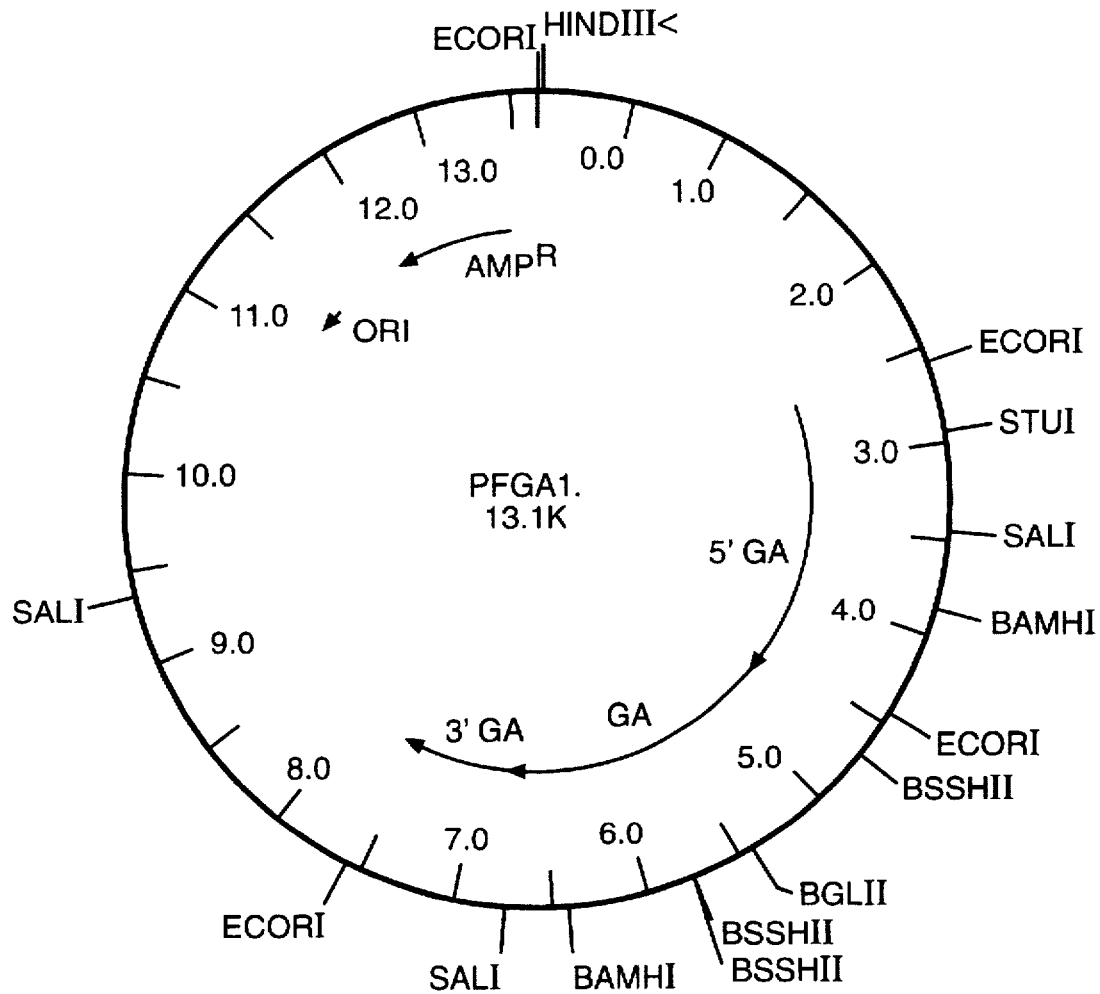
FIG._2

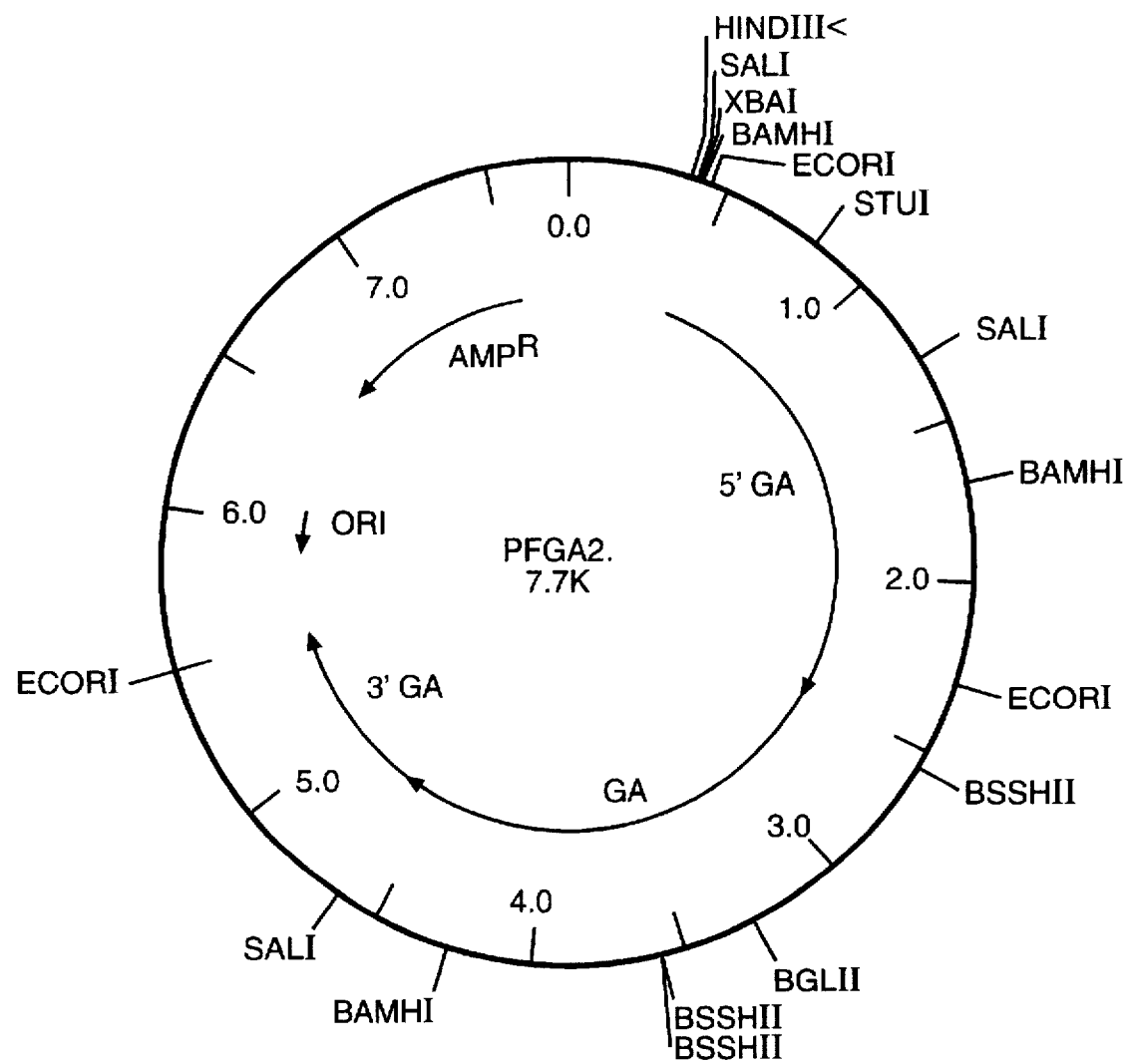
FIG._3

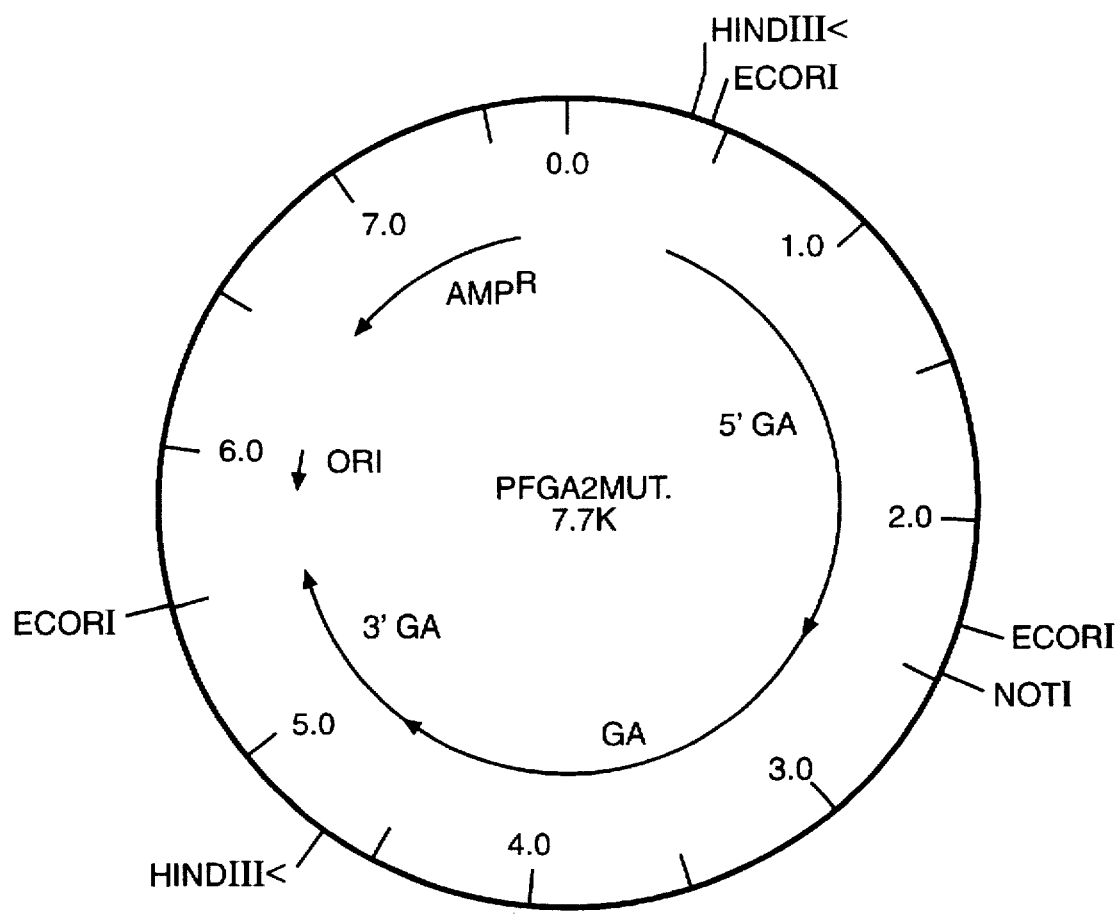
FIG._4

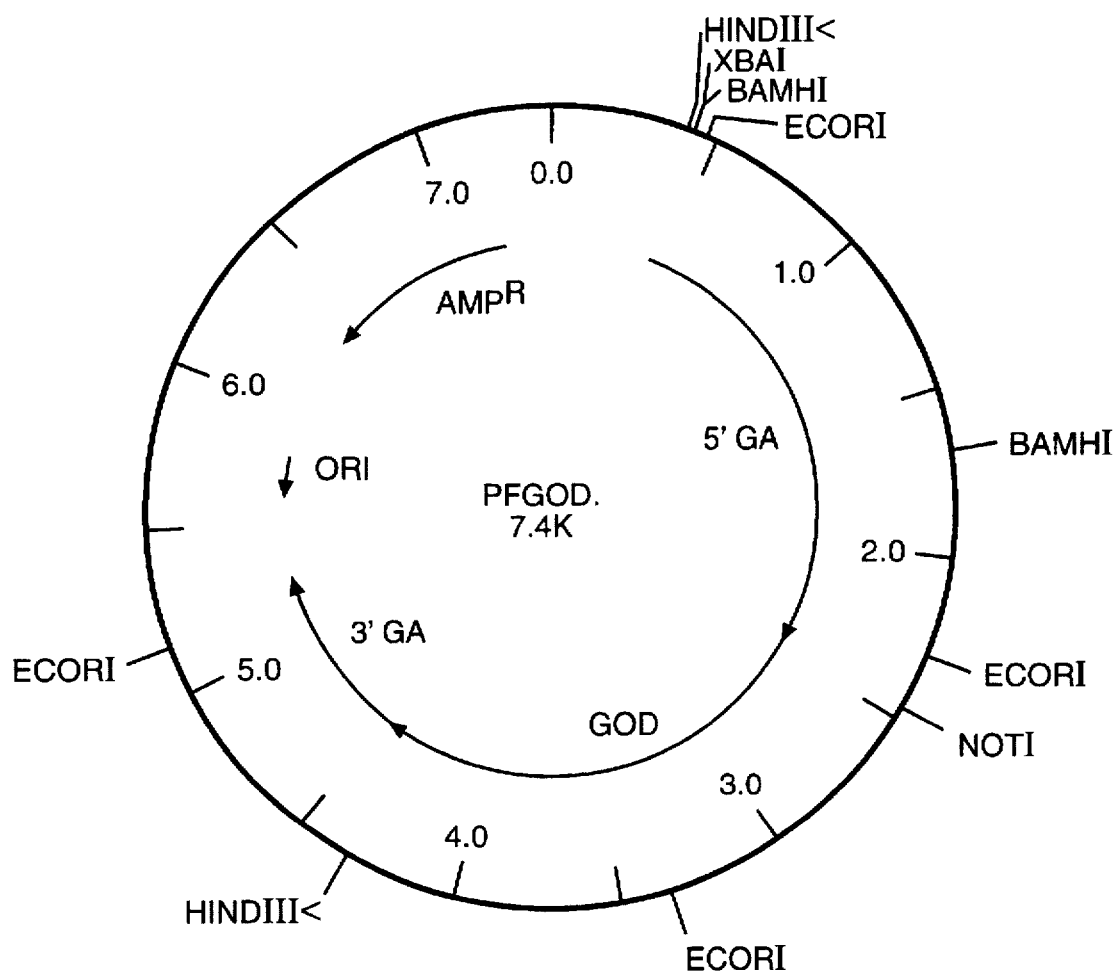
FIG._5

FIG._6A

```
                              GAATTCCCGACATCGGTCATTGGCCTCCTCG
CTGATCTCCCTTTGGTACAGTCGGCTACCAATGCTCTCGAGGATTGCCTGAACATTGACA
TTCGGCGTCCGGCCGGGACCACCGCGGACTCGAAGCTGCCTGTGCTGGTCTGGATCTTTG
GCGGAGGCTTTGAACTTGGTTCAAAGGCGATGTATGATGGTACAACGATGGTATCATCGT
CGATAGACAAGAACATGCCTATCGTGTTTGTAGCAATGAATTATCGCGTGGGAGGTTTCG
GGTTCTTGCCCGGAAAGGAGATCCTGGAGGACGGGTCCGCGAACCTAGGGCTCCTGGACC
AACGCCTTGCCCTGCAGTGGGTTGCCGACAACATCGAGGCCTTTGGTGGAGACCCGGACA
AGGTGACGATTTGGGGAGAATCAGCAGGAGCCATTCGTTTGACTAGATGACTTGTACGAC
GGAAACATCACTTACAAGGATAAGCCCTTGTTCCGGGGGGCCATCATGGACTCCGGTAGT
GTTGTTCCCGCAGACCCCGTCGATGGGGTCAAGGGACAGCAAGTATATGATGCGGTAGTG
GAATCTGCAGGCTGTTCCTCTTCTAACGACACCCTAGCTTGTCTGCGTGAACTAGACTAC
ACCGACTTCCTCAATGCGGCAAACTCCGTGCCAGGCATTTTAAGCTACCATTCTGTGGCG
TTATCATATGTGCCTCGACCGGACGGGACGGCGTTGTCGGCATCACCGGACGTTTTGGGC
AAAGCAGGGAAATATGCTCGGGTCCCGTTCATCGTGGGCGACCAAGAGGATGAGGGGACC
TTATTCGCCTTGTTTCAGTCCAACATTACGACGATCGACGAGGTGGTCGACTACCTGGCC
TCATACTTCTTCTATGACGCTAGCCGAGAGCAGCTTGAAGAACTAGTGGCCCTGTACCCA
GACACCACCACGTACGGGTCTCCGTTCAGACAGCGCGGCCAACAACTGGTATCCGCAATT
TAAGCGATTGGCCGCCATTCTCGGCGACTTGGTCTTCACCATTACCGGCGGGCATTCCTC
TCGTATGCAGAGGAAATCTCCCCTGATCTTCCGAACTGGTCGTACCTGGCGACCTATGAC
TATGGCACCCCAGTTCTGGGGACCTTCCACGGAAGTGACCTGCTGCAGGTGTTCTATGGG
ATCAAGCCAAACTATGCAGCTAGTTCTAGCCACACGTACTATCTGAGCTTTGTGTATACG
CTGGATCCGAACTCCAACCGGGGGAGTACATTGAGTGGCCGCAGTGGAAGGAATCGCGG
CAGTTGATGAATTTCGGAGCGAACGACGCCAGTCTCCTTACGGATGATTTCCGCAACGGG
ACATATGAGTTCATCCTGCAGAATACCGCGGCGTTCCACATCTGATGCCATTGGCGGAGG
GGTCCGGACGGTCAGGAACTTAGCCTTATGAGATGAATGATGGACGTGTCTGGCCTCGGA
AAAGGATATATGGGATCATGATAGTACTAGCCATATTAATGAAGGGCATATACCACGCGT
TGGACCTGCGTTATAGCTTCCCGTTAGTTATAGTACCATCGTTATACCAGCCAATCAAGT
```

CACCACGCACGACCGGGGACGGCGAATCCCCGGGAATTGAAAGAAATTGCATCCCAGGCC

AGTGAGGCAGCGATTGGCCACCTCTCCAAGGCACAGGGCCATTCTGCAGCGCTGGTGGAT

TCATCGCAATTTCCCCCGGCCCGGCCCGACACCGCTATAGGCTGGTTCTCCCACACCATC

GGAGATTCGTCGCCTAATGTCTCGTCCGTTCACAAGCTGAAGAGCTTGAAGTGGCGAGAT

GTCTCTGCAGGAATTCAAGCTAGATGCTAAGCGATATTGCATGGCAATATGTGTTGATGC

ATGTGCTTCTTCCTTCAGCTTCCCCTCGTGCAGATGAGGTTTGGCTATAAATTGAAGTGG

TTGGTCGGGGTTCCGTGAGGGGCTGAAGTGCTTCCTCCCTTTTAGACGCAACTGAGAGCC

TGAGCTTCATCCCCAGCATCATTACACCTCAGCA

*FIG._6B*

```
CAATCAATCC ATTTCGCTAT AGTTAAAGGA TGGGGATGAG GGCAATTGT TATATGATCA
TGTATGTAGT GGGTGTGCAT AATAGTAGTG AAATGGAAGC CAGTCATGTG ATTGTAATCG
ACCGACGGAA TTGAGGATAT CCGGAAATAC AGACACCGTG AAAGCCATGG TCTTTCCTTC
GTGTAGAAGA CCAGACAGAC AGTCCCTGAT TTACCCTTGC ACAAAGCACT AGAAAATTAG
CATTCCATCC TTCTCTGCTT GCTCTGCTGA TATCACTGTC ATTCAATGCA TAGCCATGAG
CTCATCTTAG ATCCAAGCAC GTAATTCCAT AGCCGAGGTC CACAGGTGAG CAGCAACATT
CCCCATCATT GCTTTCCCAG GGCCTCCCAA CGACTAAATC AAGAGTATAT CTCTACCGTC
CAATAGATCG TCTTCGCTTC AAAATCTTTG ACAATTCCAA GAGGGTCCCC ATCCATCAAA
CCCAGTTCAA TAATAGCCGA GATGCATGGT GGAGTCAATT AGGCAGTATT GCTGGAATGT
CGGGGCCAGT TCCGGTGGTC ATTGGCCGCC TGTGATGCCA TCTGCCACTA AATCCGATCA
TTGATCCACC GCCCACGAGG CGCGTCTTTG CTTTTTGCGC GGCGTCCAGG TTCAACTCTC
TCTGCAGCTC CAGTCCAACG CTGACTGACT AGTTTACCTA CTGGTCTGAT CGGCTCCATC
AGAGCTATGG CGTTATCCCG TGCCGTTGCT GCGCAATGCC TATCTTGATC GCAACCTTGA
ACTCACTCTT GTTTTAATAG TGATCTTGT GACGGAGTGT CGGTGAGTGA CAACCAACAT
CGTGCAAGGG AGATTGATAC GGAATTGTCG CTCCCATCAT GATGTTCTTG CCGGCTTTGT
TGGCCCTATC GTGGGATCGG ATGCCCTCGC TGTGCAGCAG CAGGTACTGC TGGATGAGGA
GCCATCGGTC TCTGCACGCA AACCCAACTT CCTCTTCATT CTCACGGATG ATCAGGATCT
CCGGATGAAG AATTC
```

FIG._7

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="synthetic oligonucleotide"

( x i ) SEQUENCE DESCRIPTION: SEQ ID NO:1:

```
TGATGATCAG GATCCGGCGG CCGCACCTCA GCAATGCAGA CTCTCCTTGT GAGCTCGCTT      60

GTG                                                                   63
```

( 2 ) INFORMATION FOR SEQ ID NO:2:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="synthetic oligonucleotide"

( x i ) SEQUENCE DESCRIPTION: SEQ ID NO:2:

```
GATGCTATCT TGGAAGATTA TGCTTCCATG CAGTGAGTGA AGCTTCATCG A              51
```

( 2 ) INFORMATION FOR SEQ ID NO:3:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="synthetic oligonucleotide"

( x i ) SEQUENCE DESCRIPTION: SEQ ID NO:3:

```
GATGCTATCT TGGAAGATTA TGCTTCCATG CAGTGAGTGA AGCTTCATCG A              51
```

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="synthetic oligonucleotide"

( x i ) SEQUENCE DESCRIPTION: SEQ ID NO:4:

```
GATTCATGGT TGAGCAACGA AGCGA                                           25
```

( 2 ) INFORMATION FOR SEQ ID NO:5:

( i ) SEQUENCE CHARACTERISTICS:

(A) LENGTH: 49 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="synthetic oligonucleotide"

(x i) SEQUENCE DESCRIPTION: SEQ ID NO:5:

| GCCTGAGCTT | CATCCCCAGC | GCGGCCGCAT | CATTACACCT | CAGCAATGT | 49 |

(2) INFORMATION FOR SEQ ID NO:6:

(i) SEQUENCE CHARACTERISTICS:
(A) LENGTH: 50 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="synthetic oligonucleotide"

(x i) SEQUENCE DESCRIPTION: SEQ ID NO:6:

| TGACTGACAC | CTGGCGGTGA | AAGCTTCAAT | CAATCCATTT | CGCTATAGTT | 50 |

(2) INFORMATION FOR SEQ ID NO:7:

(i) SEQUENCE CHARACTERISTICS:
(A) LENGTH: 2045 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

| GAATTCCCGA | CATCGGTCAT | TGGCCTCCTC | GCTGATCTCC | CTTTGGTACA | GTCGGCTACC | 60 |
| AATGCTCTCG | AGGATTGCCT | GAACATTGAC | ATTCGGCGTC | CGGCCGGGAC | CACCGCGGAC | 120 |
| TCGAAGCTGC | CTGTGCTGGT | CTGGATCTTT | GGCGGAGGCT | TGAACTTGG | TTCAAAGGCG | 180 |
| ATGTATGATG | GTACAACGAT | GGTATCATCG | TCGATAGACA | AGAACATGCC | TATCGTGTTT | 240 |
| GTAGCAATGA | ATTATCGCGT | GGGAGGTTTC | GGGTTCTTGC | CCGGAAAGGA | GATCCTGGAG | 300 |
| GACGGGTCCG | CGAACCTAGG | GCTCCTGGAC | CAACGCCTTG | CCCTGCAGTG | GGTTGCCGAC | 360 |
| AACATCGAGG | CCTTTGGTGG | AGACCCGGAC | AAGGTGACGA | TTTGGGGAGA | ATCAGCAGGA | 420 |
| GCCATTCGTT | TGACTAGATG | ACTTGTACGA | CGGAAACATC | ACTTACAAGG | ATAAGCCCTT | 480 |
| GTTCCGGGGG | GCCATCATGG | ACTCCGGTAG | TGTTGTTCCC | GCAGACCCCG | TCGATGGGGT | 540 |
| CAAGGGACAG | CAAGTATATG | ATGCGGTAGT | GGAATCTGCA | GGCTGTTCCT | CTTCTAACGA | 600 |
| CACCCTAGCT | TGTCTGCGTG | AACTAGACTA | CACCGACTTC | CTCAATGCGG | CAAACTCCGT | 660 |
| GCCAGGCATT | TTAAGCTACC | ATTCTGTGGC | GTTATCATAT | GTGCCTCGAC | CGGACGGGAC | 720 |
| GGCGTTGTCG | GCATCACCGG | ACGTTTGGG | CAAAGCAGGG | AAATATGCTC | GGGTCCCGTT | 780 |
| CATCGTGGGC | GACCAAGAGG | ATGAGGGGAC | CTTATTCGCC | TTGTTTCAGT | CCAACATTAC | 840 |
| GACGATCGAC | GAGGTGGTCG | ACTACCTGGC | CTCATACTTC | TTCTATGACG | CTAGCCGAGA | 900 |
| GCAGCTTGAA | GAACTAGTGG | CCCTGTACCC | AGACACCACC | ACGTACGGGT | CTCCGTTCAG | 960 |
| ACAGCGCGGC | CAACAACTGG | TATCCGCAAT | TAAGCGATT | GGCCGCCATT | CTCGGCGACT | 1020 |
| TGGTCTTCAC | CATTACCGGC | GGGCATTCCT | CTCGTATGCA | GAGGAAATCT | CCCCTGATCT | 1080 |
| TCCGAACTGG | TCGTACCTGG | CGACCTATGA | CTATGGCACC | CCAGTTCTGG | GGACCTTCCA | 1140 |
| CGGAAGTGAC | CTGCTGCAGG | TGTTCTATGG | GATCAAGCCA | AACTATGCAG | CTAGTTCTAG | 1200 |

| | | | | | | |
|---|---|---|---|---|---|---|
| CCACACGTAC | TATCTGAGCT | TTGTGTATAC | GCTGGATCCG | AACTCCAACC | GGGGGGAGTA | 1260 |
| CATTGAGTGG | CCGCAGTGGA | AGGAATCGCG | GCAGTTGATG | AATTTCGGAG | CGAACGACGC | 1320 |
| CAGTCTCCTT | ACGGATGATT | TCCGCAACGG | GACATATGAG | TTCATCCTGC | AGAATACCGC | 1380 |
| GGCGTTCCAC | ATCTGATGCC | ATTGGCGGAG | GGGTCCGGAC | GGTCAGGAAC | TTAGCCTTAT | 1440 |
| GAGATGAATG | ATGGACGTGT | CTGGCCTCGG | AAAAGGATAT | ATGGGATCAT | GATAGTACTA | 1500 |
| GCCATATTAA | TGAAGGGCAT | ATACCACGCG | TTGGACCTGC | GTTATAGCTT | CCCGTTAGTT | 1560 |
| ATAGTACCAT | CGTTATACCA | GCCAATCAAG | TCACCACGCA | CGACCGGGGA | CGGCGAATCC | 1620 |
| CCGGGAATTG | AAAGAAATTG | CATCCCAGGC | CAGTGAGGCA | GCGATTGGCC | ACCTCTCCAA | 1680 |
| GGCACAGGGC | CATTCTGCAG | CGCTGGTGGA | TTCATCGCAA | TTTCCCCCGG | CCCGGCCCGA | 1740 |
| CACCGCTATA | GGCTGGTTCT | CCCACACCAT | CGGAGATTCG | TCGCCTAATG | TCTCGTCCGT | 1800 |
| TCACAAGCTG | AAGAGCTTGA | AGTGGCGAGA | TGTCTCTGCA | GGAATTCAAG | CTAGATGCTA | 1860 |
| AGCGATATTG | CATGGCAATA | TGTGTTGATG | CATGTGCTTC | TTCCTTCAGC | TTCCCTCGT | 1920 |
| GCAGATGAGG | TTTGGCTATA | AATTGAAGTG | GTTGGTCGGG | GTTCCGTGAG | GGGCTGAAGT | 1980 |
| GCTTCCTCCC | TTTTAGACGC | AACTGAGAGC | CTGAGCTTCA | TCCCCAGCAT | CATTACACCT | 2040 |
| CAGCA | | | | | | 2045 |

(2) INFORMATION FOR SEQ ID NO:8:

(i) SEQUENCE CHARACTERISTICS:
   (A) LENGTH: 1035 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:8:

| | | | | | | |
|---|---|---|---|---|---|---|
| CAATCAATCC | ATTTCGCTAT | AGTTAAAGGA | TGGGGATGAG | GGCAATTGGT | TATATGATCA | 60 |
| TGTATGTAGT | GGGTGTGCAT | AATAGTAGTG | AAATGGAAGC | CAGTCATGTG | ATTGTAATCG | 120 |
| ACCGACGGAA | TTGAGGATAT | CCGGAAATAC | AGACACCGTG | AAAGCCATGG | TCTTTCCTTC | 180 |
| GTGTAGAAGA | CCAGACAGAC | AGTCCCTGAT | TTACCCTTGC | ACAAAGCACT | AGAAAATTAG | 240 |
| CATTCCATCC | TTCTCTGCTT | GCTCTGCTGA | TATCACTGTC | ATTCAATGCA | TAGCCATGAG | 300 |
| CTCATCTTAG | ATCCAAGCAC | GTAATTCCAT | AGCCGAGGTC | CACAGGTGAG | CAGCAACATT | 360 |
| CCCCATCATT | GCTTTCCCAG | GGCCTCCCAA | CGACTAAATC | AAGAGTATAT | CTCTACCGTC | 420 |
| CAATAGATCG | TCTTCGCTTC | AAAATCTTTG | ACAATTCCAA | GAGGGTCCCC | ATCCATCAAA | 480 |
| CCCAGTTCAA | TAATAGCCGA | GATGCATGGT | GGAGTCAATT | AGGCAGTATT | GCTGGAATGT | 540 |
| CGGGGCCAGT | TCCGGTGGTC | ATTGGCCGCC | TGTGATGCCA | TCTGCCACTA | AATCCGATCA | 600 |
| TTGATCCACC | GCCCACGAGG | CGCGTCTTTG | CTTTTTGCGC | GGCGTCCAGG | TTCAACTCTC | 660 |
| TCTGCAGCTC | CAGTCCAACG | CTGACTGACT | AGTTTACCTA | CTGGTCTGAT | CGGCTCCATC | 720 |
| AGAGCTATGG | CGTTATCCCG | TGCCGTTGCT | GCGCAATCGC | TATCTTGATC | GCAACCTTGA | 780 |
| ACTCACTCTT | GTTTTAATAG | TGATCTTGGT | GACGGAGTGT | CGGTGAGTGA | CAACCAACAT | 840 |
| CGTGCAAGGG | AGATTGATAC | GGAATTGTCG | CTCCCATCAT | GATGTTCTTG | CCGGCTTTGT | 900 |
| TGGCCCTATC | GTGGGATCGG | ATGCCCTCGC | TGTGCAGCAG | CAGGTACTGC | TGGATGAGGA | 960 |
| GCCATCGGTC | TCTGCACGCA | AACCCAACTT | CCTCTTCATT | CTCACGGATG | ATCAGGATCT | 1020 |
| CCGGATGAAG | AATTC | | | | | 1035 |

EXPRESSION SYSTEM, INTEGRATION VECTOR AND CELL TRANSFORMED BY THIS INTEGRATION VECTOR

The invention relates to an expression system which is usable for the production of glucose oxidase and, more especially, capable of effecting the extra-cellular production of glucose oxidase.

The invention also relates to an integration vector containing this expression system, and to a cell transformed by this integration vector.

Glucose oxidase is classified in the international system under the reference E.C. 1.1.3.4. or β-D-glucose:oxygen 1-oxidoreductase. This enzyme catalyses the oxidation reaction of β-D-glucose to D-glucono-δ-lactone, which is then hydrolysed to gluconic acid. This reaction produces hydrogen peroxide, which is converted to oxygen and water by the action of the catalase produced by wild-type Aspergillus strains.

Glucose oxidase is naturally produced by some strains of filamentous fungi, and in particular by Aspergillus strains. Unfortunately, the glucose oxidase produced by these Aspergillus strains is not secreted effectively into the culture medium of these strains, the glucose oxidase not passing through the cell wall (WITTE-VEEN C. F. B. et al., Applied and Environmental Microbiology, 1992, 58 (4), pages 1190–1194). Industrially, glucose oxidase is hence treated as an intracellular enzyme. The Aspergillus cells have to be disrupted prior to the recovery and purification of the glucose oxidase. The additional step of cell disruption before harvesting imposes constraints, is difficult to carry out industrially and, moreover, gives rise to quite considerable falls in yield. In effect, after disruption of the cells, the aqueous suspension obtained contains glucose oxidase in solution together with other enzymes and polypeptides, but also many more or less soluble cell constituents. A purification step entailing several separation operations is hence essential for obtaining pure or industrially usable glucose oxidase. For this reason, an extracellular production of glucose oxidase, that is to say secretion of the enzyme into the culture medium, has been sought for a long time.

Moreover, a method of production of glucose oxidase in which catalase would be present in only minimal amounts in the medium has been sought for a long time. The object of this is to prevent the hydrogen peroxide formed in the glucose oxidase-catalysed reaction from being degraded to oxygen and water by the catalase present in the medium.

In this context, the proposal is made in Patent Application WO 89/12,675 to transform a yeast with a plasmid. This plasmid contains the promoter sequence of a yeast dehydrogenase (ADH2-GAP), the *Aspergillus niger* glucose oxidase secretion signal sequence or the *Saccharomyces cerevisiae* α-mating factor secretion signal sequence, the mature sequence of Aspergillus niger glucose oxidase and the terminator of a yeast dehydrogenase (GAP). The transformed yeast (*Saccharomyces cerevisiae*) secretes glucose oxidase.

In European Patent Application 0,357,127, an expression system which is usable for the production of bovine chymosin is described. This expression system comprises the *Aspergillus niger* glucoamylase promoter sequence, the *Aspergillus niger* glucoamylase signal peptide sequence, the bovine chymosin coding sequence and the *Aspergillus niger* glucoamylase terminator sequence. A transformed strain of *Aspergillus niger* containing this expression system enables bovine chymosin to be obtained.

At the present time, an expression system making it possible to obtain the expression and an effective secretion of glucose oxidase by a transformed strain of filamentous fungus containing this expression system is not known.

The primary object of the present invention is to provide an expression system enabling glucose oxidase to be obtained in the culture medium in which the transformed strain containing this expression system is cultured. This expression system enables a substantially extracellular production of glucose oxidase to be obtained. This expression system makes it possible, furthermore, to obtain an enzyme composition containing glucose oxidase virtually without catalase.

Glucose oxidase is understood to mean an enzyme which catalyses the oxidation reaction of β-D-glucose to D-glucono-δ-lactone, which is then hydrolysed to gluconic acid. This enzyme is classified in the international system under the reference E.C. 1.1.3.4. or β-D-glucose: oxygen 1-oxidoreductase. This definition includes the natural enzymes and modified enzymes, such as enzymes whose nucleotide or amino acid sequence has been modified by genetic engineering techniques or by mutagenesis techniques.

The object of the present invention is also to provide an integration vector and a plasmid containing the expression system described above.

The object of the present invention is also to provide a strain transformed by the integration vector or the plasmid described above, especially a transformed strain of Aspergillus, and more especially a transformed strain of *Aspergillus foetidus*, which expresses glucose oxidase and secretes it into its culture medium with a high level of productivity. The secretion of glucose oxidase by this transformed strain is substantially extracellular.

The object of the present invention is also to provide a process for producing glucose oxidase employing a strain of filamentous fungus which produces a large amount of glucose oxidase and secretes it almost completely extracellularly.

To this end, the invention relates to an expression system which is usable for the extracellular production of glucose oxidase, characterized in that it comprises at least:

the sequence of a promoter, the glucose oxidase secretion signal sequence, and the mature glucose oxidase sequence.

Usually, the expression system also comprises the sequence of a terminator. In a preferred variant, the sequence of a promoter is the glucoamylase promoter sequence.

The invention relates to an expression system which is usable for the production of glucose oxidase, characterized in that it comprises at least:

the *Aspergillus foetidus* glucoamylase promoter sequence, the *Aspergillus foetidus* glucose oxidase secretion signal sequence, the mature sequence of *Aspergillus foetidus* glucose oxidase, and the *Aspergillus foetidus* glucoamylase terminator sequence.

Expression system is understood to mean a molecular unit integrated in the genome of a filamentous fungus and capable of providing this fungus with the genetic information needed for the biosynthesis of glucose oxidase.

Promoter is understood to mean the transcription promoter(s). The promoter which consists of a DNA sequence showing strong transcriptional activity may be preceded by DNA sequences which stimulate transcription, such as sequences known by the name of "enhancers" or "upstream activating sequences". The promoter contains transcription control sequences which influence the expression of the fused coding DNA. The gene promoter sequence comprises the sequences which control transcription and which participate during the expression of gene.

Usually, the promoter sequence originates from a filamentous fungus. Generally, it originates from an Aspergillus strain. Preferably, it originates from an *Aspergillus niger, Aspergillus foetidus, Aspergillus awamori* or *Aspergillus oryzae* strain. As a special preference, it originates from an *Aspergillus niger* strain or from an *Aspergillus foetidus* strain. *Aspergillus niger* strains and *Aspergillus foetidus* strains from which the glucoamylase promoter sequence can originate are known, such as, in particular, *Aspergillus niger* strain NRRL 3 (AGRICULTURAL RESEARCH SERVICE CULTURE COLLECTION (NRRL), 1815 North University Street, Peoria, Ill. 61604, USA), Aspergillus niger strain ATCC 13496 (AMERICAN TYPE CULTURE COLLECTION, 12301 Parklawn Drive, Rockville, Md. 20852-1776, USA), *Aspergillus niger* strain ATCC 22343, *Aspergillus niger* strain ATCC 46890, *Aspergillus foetidus* strain ATCC 10254 and *Aspergillus foetidus* strain ATCC 14916. Preferably the glucoamylase promoter sequence originates from an *Aspergillus foetidus* strain. As a special preference, it originates from *Aspergillus foetidus* strain SE4. The DNA molecule comprising the nucleotide sequence SEQ ID NO:7 codes for the *Aspergillus foetidus* strain SE4 promoter.

The invention also relates to the *Aspergillus foetidus* glucoamylase promoter. More especially, the invention relates to a DNA molecule comprising the nucleotide sequence SEQ ID NO:7 which codes for the *Aspergillus foetidus* SE4 glucoamylase promoter.

Glucose oxidase secretion signal sequence is understood to mean a DNA sequence corresponding to an amino acid sequence which is naturally linked operationally to the amino terminus of the mature glucose oxidase sequence. The gene coding for glucose oxidase has been cloned and sequenced, and the amino acid sequence which has been deduced from this study shows the presence of a presequence having some features of a signal peptide, but which are more complex (WHITTINGTON H. et al., Curr. Genet., 18 (1990), pages 531–536). For this reason, in this application, the portion of the structural gene which codes for the supposed signal peptide is designated "glucose oxidase secretion signal sequence", and the portion of structural gene which codes for glucose oxidase as such is designated "mature glucose oxidase sequence".

Usually, the glucose oxidase secretion signal sequence originates from a strain of filamentous fungus. Generally, it originates from an Aspergillus strain or from a Penicillium strain. Preferably, it originates from an Aspergillus strain such as, in particular, an *Aspergillus niger, Aspergillus foetidus, Aspergillus awamori* or *Aspergillus oryzae* strain. As a special preference, it originates from an *Aspergillus niger* strain or from an *Aspergillus foetidus* strain. Good results have been obtained with the glucose oxidase secretion signal sequence of *Aspergillus niger* strain NRRL 3 (AGRICULTURAL RESEARCH SERVICE CULTURE COLLECTION (NRRL), 1815 North University Street, Peoria, Ill. 61604, USA). This sequence has been published in The Journal of Biological Chemistry, 1990, 265 (7), pages 3793–3802. Good results have also been obtained with the glucose oxidase secretion signal sequence of *Aspergillus foetidus* strain ATCC 14916 (AMERICAN TYPE CULTURE COLLECTION, 12301 Parklawn Drive, Rockville, Md. 20852-1776, USA).

The expression system according to the invention comprises the mature glucose oxidase sequence. Mature glucose oxidase sequence is understood to mean the portion of the sequence which is translated into active protein, that is to say the glucose oxidase coding sequence which corresponds to the glucose oxidase structural gene without the secretion signal sequence. The coding sequence (structural gene) comprises the secretion signal sequence and the mature glucose oxidase sequence.

Usually, the mature glucose oxidase sequence originates from a strain of filamentous fungus. Generally, it originates from an Aspergillus strain or from a Penicillium strain. Preferably, it originates from an Aspergillus strain such as, in particular, an *Aspergillus niger, Aspergillus foetidus, Aspergillus awamori* or *Aspergillus oryzae* strain. As a special preference, it originates from an *Aspergillus niger* strain or from an *Aspergillus foetidus* strain. Good results have been obtained with the mature glucose oxidase sequence of *Aspergillus niger* strain NRRL 3. This sequence has been published in The Journal of Biological Chemistry, 1990, 265 (7), pages 3793–3802. Good results have also been obtained with the mature glucose oxidase sequence of *Aspergillus foetidus* strain ATCC 14916 (AMERICAN TYPE CULTURE COLLECTION).

In a preferred variant of the invention, the glucose oxidase secretion signal sequence and the mature glucose oxidase sequence originate from the same filamentous fungus. Excellent results have been obtained with an expression system according to the invention comprising the glucose oxidase secretion signal sequence of *Aspergillus foetidus* strain ATCC 14916 and the mature glucose oxidase sequence of *Aspergillus foetidus* strain ATCC 14916. Excellent results have also been obtained with an expression system according to the invention comprising the glucose oxidase secretion signal sequence of *Aspergillus niger* strain NRRL 3 and the mature glucose oxidase sequence of *Aspergillus niger* strain NRRL 3.

Terminator is understood to be the transcription terminator(s). The terminator sequence of a gene is a DNA sequence which acts to terminate the transcription of this gene. The terminator sequence also contains polyadenylation signal which stabilizes the mRNA.

Usually, the terminator sequence originates from a filamentous fungus. In this application, any terminator which is functional in a filamentous fungus can be suitable. Terminators are known to a person skilled in the art. As examples of a known terminator of fungal origin, there may be mentioned the trpC terminator, that of a glucoamylase, that of an amylase, that of an alpha-amylase, that of an aspartic protease, that of an acid phosphatase, that of a lipase, that of a cellulase, that of a glycolytic enzyme, that of a glucanase, that of a hydrolase and that of a dehydrogenase, and especially the *Aspergillus nidulans* trpc terminator, the *Aspergillus niger* glucoamylase terminator, that of *Aspergillus niger* alpha-amylase, that of *Mucor miehei* aspartic protease, that of *Aspergillus niger* acid phosphatase and that of an *Aspergillus nidulans* alcohol dehydrogenase. Generally, the terminator sequence originates from an Aspergillus strain. Preferably, it originates from an *Aspergillus niger, Aspergillus foetidus, Aspergillus awamori* or *Aspergillus oryzae* strain. As a special preference, it originates from an *Aspergillus niger* strain or from an *Aspergillus foetidus* strain. In a preferred variant, the terminator sequence is the glucoamylase terminator sequence. Preferably, the glucoamylase terminator sequence originates from an *Aspergillus foetidus* strain. As a special preference, it originates from *Aspergillus foetidus* strain SE4. The DNA molecule comprising the nucleotide sequence SEQ ID NO:8 codes for the *Aspergillus foetidus* strain SE4 terminator.

The invention also relates to the *Aspergillus foetidus* glucoamylase terminator. More especially, the invention relates to a DNA molecule comprising the nucleotide sequence SEQ ID NO:8 which codes for the *Aspergillus foetidus* SE4 glucoamylase terminator.

In a preferred variant of the invention, the glucoamylase promoter sequence and the glucoamylase terminator sequence originate from the same filamentous fungus. Good results have been obtained with an expression system according to the invention comprising a *Aspergillus foetidus* strain glucoamylase promoter sequence and a *Aspergillus foetidus* strain glucoamylase terminator sequence. Excellent results have been obtained with an expression system according to the invention comprising the *Aspergillus foetidus* strain SE4 glucoamylase promoter sequence and the *Aspergillus foetidus* strain SE4 glucoamylase terminator sequence.

Preferably, in the expression system according to the invention, the promoter sequence is positioned upstream of the secretion signal sequence, which is itself positioned upstream of the mature sequence; this mature sequence is positioned upstream of the terminator sequence. These positionings are chosen in such a way that, under suitable conditions, they permit the expression of glucose oxidase under the control of the transcription signals, that is to say of the promoter and the terminator.

Preferably, the sequences included in the expression system are linked operationally. The promoter sequence is linked operationally to the glucose oxidase secretion signal sequence. The glucose oxidase secretion signal sequence is linked operationally to the mature glucose oxidase sequence. The mature glucose oxidase sequence is linked operationally to the terminator sequence.

The invention also relates to a process for preparing an expression system comprising at least the sequence of a promoter, the glucose oxidase secretion signal sequence, the mature glucose oxidase sequence and the sequence of a terminator. This process comprises:

isolation of the glucose oxidase secretion signal sequence and of the mature glucose oxidase sequence from the genomic DNA of a microorganism which produces this glucose oxidase, and introduction of the glucose oxidase secretion signal sequence and the mature glucose oxidase sequence into a vector containing the sequence of a promoter and the sequence of a terminator, this introduction being done into a site chosen in such a way that the positioning of the sequences permits the expression of glucose oxidase under the control of the said promoter and said terminator.

The invention also relates to an integration vector containing the expression system as defined above, and which is capable of permitting the expression of glucose oxidase.

The principle of the invention also applies to an expression vector containing the expression system as defined above, and which is capable of permitting the expression of glucose oxidase.

Integration vector is understood to mean any DNA sequence which comprises a complete gene expression unit. Complete gene expression unit is understood to mean the structural gene and the region(s) of the promoter and the region(s) of regulation which is needed for transcription and translation. Structural gene is understood to mean the coding sequence which is used for transcription into RNA and enables the host to synthesize the protein.

Preferably, this integration vector is a plasmid. Good results have been obtained with plasmid pFGOD.

The invention also relates to a transformed cell (host cell), transformed by the integration vector defined above. This transformed cell is chosen in such a way that the promoter sequence and the terminator sequence included in the expression system are recognized by this transformed cell, that is to say they are compatible and functional for this transformed cell, the promoter sequence and the terminator sequence included in the expression system carry out their respective transcription signal functions as a promoter and a terminator, respectively, for the transformed cell.

Usually, the transformed cell is a cell of a filamentous fungus. Generally, the transformed cell is an Aspergillus cell. As a special preference, the transformed cell is an *Aspergillus niger, Aspergillus foetidus, Aspergillus awamori* or *Aspergillus oryzae* cell. Good results have been obtained with a transformed *Aspergillus niger* cell, and more especially with a transformed *Aspergillus niger* strain NRRL 3 cell. Excellent results have been obtained with a transformed *Aspergillus foetidus* cell, and more especially with a transformed *Aspergillus foetidus* strain SE4 cell.

In a preferred variant of the invention, the cell transformed by the integration vector is derived from the strain from which the promoter sequence and/or the terminator sequence, a sequence included in the expression system, originates. Excellent results have been obtained with a transformed *Aspergillus foetidus* SE4 cell. This cell transformed by an integration vector contains an expression system according to the invention, this expression system comprising a *Aspergillus foetidus* SE4 promoter sequence and a *Aspergillus foetidus* SE4 terminator sequence, and more especially the *Aspergillus foetidus* SE4 glucoamylase promoter sequence and the *Aspergillus foetidus* SE4 glucoamylase terminator sequence. Best results have been obtained with a cell transformed by the integration vector pFGOD.

Filamentous fungus is understood to mean the eukaryotic microorganisms which comprise all the filamentous forms of the division Eumycota. In this division are included the groups Zygomycetes, Ascomycetes, Basidiomycetes and imperfect fungi including Hyphomycetes. The following genera are included in this definition: Aspergillus, Trichoderma, Neurospora, Podospora, Endothia, Mucor, Cochiobolus, Pyricularia, Penicillium and Humicola.

The invention also relates to purified and isolated *Aspergillus foetidus* strain SE4tr. This transformed strain SE4tr is obtained from the strain SE4. It differs from this strain SE4 in that it contains one or more copies of plasmid pFGOD integrated in its genome.

*Aspergillus foetidus* strain SE4 was obtained from *Aspergillus foetidus* strain ATCC 14916 by mutagenesis, and selected on the basis of an improved production of glucoamylase.

The name *Aspergillus foetidus* is synonymous with *Aspergillus citricus* (ATCC Names of Industrial Fungi, 1994, p. 120, published by the American Type Culture Collection).

The invention also relates to a process for the extracellular production of glucose oxidase, characterized in that it comprises the following steps:

transformation of a cell with an integration vector containing an expression system as defined above, under conditions permitting the expression and secretion of glucose oxidase, culturing of the transformed cell in an appropriate culture medium, and recovery of the secreted glucose oxidase.

The fermentation medium obtained after culturing the transformed cell contains most of the glucose oxidase. In effect, glucose oxidase is substantially secreted into the culture medium by the transformed strain. The glucose oxidase obtained by the process of the invention is extracellular.

The fermentation medium obtained after culturing the transformed cell contains virtually no catalase. This enables an enzyme composition containing glucose oxidase substantially without catalase to be obtained.

The invention also relates to the glucose oxidase produced by a transformed cell as defined above.

Glucose oxidase has many industrial applications, such as, for example, in the food industries, pharmaceutical industries and chemical industries.

It is, in particular, employed for measuring the blood glucose level, and can be incorporated for this application in a diagnostic kit. The glucose oxidase obtained according to the invention possesses an advantage in this application since it is not contaminated with catalase.

Glucose oxidase can be used to measure glucose and oxygen concentration.

Glucose oxidase may be used as an antioxidant, to remove oxygen or glucose, in particular in some food products or some drinks.

Glucose oxidase may also be introduced into toothpastes for preventing caries.

Glucose oxidase has been incorporated in some paints in order to prevent corrosion.

BRIEF DESCRIPTION OF THE DRAWINGS

FIG. 1 shows the restriction map of plasmid pUCGOD.

FIG. 2 shows the restriction map of plasmid pFGA1.

FIG. 3 shows the restriction map of plasmid pFGA2.

FIG. 4 shows the restriction map of plasmid pFGA2MUT.

FIG. 5 shows the restriction map of plasmid pFGOD.

FIG. 6 (FIG. 6a and FIG. 6b) shows the nucleotide sequence (SEQ ID NO:7) coding for the *Aspergillus foetidus* SE4 glucoamylase promoter.

FIG. 7 shows the nucleotide sequence (SEQ ID NO:8) coding for the *Aspergillus foetidus* SE4 glucoamylase terminator.

The symbols and abbreviations used in these figures are explained in Table 1.

TABLE 1

| Symbol Abbreviation | Meaning |
|---|---|
| AMPR | gene providing resistance to ampicillin |
| ORI | origin of replication in *E. coli* |
| GOD | *Aspergillus foetidus* ATCC 14916 glucose oxidase coding sequence |
| 5' GA | *Aspergillus foetidus* SE4 glucoamylase promoter |
| 3' GA | *Aspergillus foetidus* SE4 glucoamylase terminator |

TABLE 1-continued

| Symbol Abbreviation | Meaning |
|---|---|
| GA | *Aspergillus foetidus* SE4 glucoamylase coding sequence |

The present invention is illustrated by the examples which follow.

EXAMPLE 1

Isolation of the *Aspergillus foetidus* ATCC 14916 glucose oxidase coding sequence An *Aspergillus foetidus* strain ATCC 14916 culture is prepared on an ACM ("Aspergillus Complete Medium") liquid nutrient medium containing 2% (weight/volume) of malt extract, 0.1% (weight/volume) of peptone (DIFCO) and 2% (weight/volume) of glucose. After incubation for 48 hours at 32° C., the mycelium is harvested.

*Aspergillus foetidus* strain ATCC 14916 genomic DNA is isolated according to the technique described in GARBER, R. C. and YODER, O. L., Anal. Biochem. 135 (1983), pages 416–422.

The following mixture is prepared:

| Distilled H$_2$O | 62 µl |
|---|---|
| PCR buffer (10x) | 10 µl |
| dNTPs (2.5 mM each) | 8 µl |
| Oligonucleotide SEQ ID NO: 1 (20 µM) | 5 µl |
| Oligonucleotide SEQ ID NO: 2 (20 µM) | 5 µl |
| Genomic DNA (dilutions 10$^{-1}$ to 10$^{-4}$) | 10 µl |
| Taq polymerase (5 U/µl) | 0.2 µl |

The PCR buffer, referred to as "(10×) Reaction Buffer composition", the abbreviation dNTPs which means all the nucleotides DATP, dTTP, dGTP and dCTP, and the product Taq polymerase are described in the leaflet of the kit sold under the name "GENEAMP DNA AMPLIFICATION REAGENT KIT with AMPLITAQ Recombinant Taq DNA Polymerase" (PERKIN ELMER CETUS).

The genomic DNA isolated from *Aspergillus foetidus* strain ATCC 14916 is employed in this mixture at a concentration of 1 µg/µl.

The *Aspergillus foetidus* ATCC 14916 glucose oxidase coding sequence was isolated according to the PCR technique ("Polymerase Chain Reaction" technique described in SAIKI, R. K., et al., SCIENCE, 239 (1988), pages 487–491).

The sequences of the synthetic oligonucleotides employed in this study are as follows: SEQ ID NO:1

SEQ ID NO: 1

5' - TGATGATCAGGATCCGGCGGCCGCACCTCAGCAATGCAGACTCTCCTTGTGAGCTCGCTTGTG - 3'
         BamHI      NotI

SEQ ID NO: 2

5' - TCGATGAAGCTTCACTCACTGCATGGAAGCATAATCTTCCAAGATAGCATC - 3'

SEQ ID NO: 3

5' - GATGCTATCTTGGAAGATTATGCTTCCATGCAGTGAGTGAAGCTTCATCGA - 3'
                                                HindIII The sequence SEQ ID NO:2 is the complement of the sequence SEQ ID NO:3.

The sequence of the oligonucleotide SEQ ID NO:1 contains the information for the BamHI and NotI restriction sites, the information for the untranslated 5' region of *Aspergillus foetidus* SE4 glucoamylase and the beginning of the glucose oxidase coding sequence.

The sequence of the oligonucleotide SEQ ID NO:2 and its complement, the oligonucleotide SEQ ID NO:3, contain the nucleotides which correspond to the end of the glucose oxidase coding sequence and the additional information for the HindIII restriction site.

The technique used to construct the synthetic oligonucleotides is described in BEAUCAGE, S. L. et al. (1981), Tetrahedron Letters, 22, pages 1859–1882, using β-cyanoethyl phosphoramidites in a BIOSEARCH CYCLONE SYNTHESIZER apparatus.

The conditions followed for PCR are as follows: 2 minutes at 95° C., then 30 cycles of a series comprising 1 minute at 95° C., 1 minute at 60° C. and 2 minutes at 72° C., then 10 minutes at 72° C., then a temperature of 20° C. is maintained. All the other parameters used for this PCR correspond to those described in the leaflet of the kit sold under the name "GENEAMP DNA AMPLIFICATION REAGENT KIT with AMPLITAQ Recombinant Taq DNA Polymerase" (PERKIN ELMER CETUS).

An approximately 1.8-kb DNA fragment (1 kg =1000 base pairs) was isolated as described above. It was compared using the restriction analysis technique (analysis described in Molecular Cloning—a laboratory manual—MANIATIS et al., (Cold Spring Harbor Laboratory) 1982, pages 374–379) with the sequence published in The Journal of Biological Chemistry, 1990, 265 (7), pages 3793–3802. No essential difference was found.

The DNA fragment thereby obtained is digested with the restriction enzymes BamHI and HindIII and is then ligated, according to the ligation technique described in Molecular Cloning—a laboratory manual—SAMBROOK et al.— second edition, 1989, pages 1.68–1.69, with plasmid pUC18 (CLONTECH Laboratories, No. 6110-1) which has previously been digested at the BamHI and HindIII sites. The vector pUCGOD (FIG. 1) is thereby obtained.

EXAMPLE 2
Construction of plasmid pFGA2MUT

Plasmid pFGA2MUT (FIG. 4) contains the *Aspergillus foetidus* SE4 glucoamylase gene in which a NotI cloning site has been created between the promoter and the coding portion of the glucoamylase gene, and a HindIII cloning site between the coding portion and the terminator of the glucoamylase gene. These two cloning sites, NotI and HindIII, are created by mutagenesis as described below.

*Aspergillus foetidus* SE4 glucoamylase gene is isolated according to the following description.

*Aspergillus foetidus* strain SE4 chromosomal DNA is isolated according to the technique of GARBER et al. as described in Example 1. This isolated chromosomal DNA is partially digested with the restriction enzyme SauIIIA, and fragments 8 to 10 kb in size are isolated and purified with a sucrose gradient (15 to 40%) according to the technique described in AUSUBEL, F. M. et al. (1989), Current Protocols in Molecular Biology (John WILLEY and Sons), pages 5.3.2–5.3.8. These isolated and purified fragments are introduced into plasmid pBR322 (CLONTECH LABORATORIES catalogue No. 6210-1), which has previously been digested with the restriction enzyme BamHI. *E. coli* strain DH5α (described by HANAHAN, D., J. Mol. Biol. (1983) 166, pages 557–580 and sold by BETHESDA RESEARCH LABORATORIES (BRL), B.R.L. Focus (1986) 8, page 9) is then transformed.

Approximately 15,000 transformed *E. coli* clones are screened by means of the hybridization technique (SAMBROOK et al., pages 9.52–9.55) using the following synthetic oligonucleotide (SEQ ID NO:4):

5'-GATTCATGGTTGAGCAACGAAGCGA-3'

The choice is based on the glucoamylase nucleotide sequence published by BOEL et al., EMBO J. 3 (1984), pages 1097–1102.

A colony which hybridizes with this oligonucleotide is isolated. The restriction sites are analysed, and it is found that this strain contains the complete glucoamylase gene, that is to say the promoter, the terminator and the coding region as well as the secretion signal.

The 8.7-kb fragment was introduced as described above into plasmid pBR322 at the BamHI site.

The vector PFGA1 (FIG. 2), which contains an 8.7-kb insert of Aspergillus DNA, is thereby created. This insert is the only difference between plasmid pBR322 and the vector pFGA1.

A plasmid which is derived from the vector pFGA1 and which contains a smaller insert than that of the vector pFGA1 is constructed as follows. The vector pFGA1 is digested with the restriction enzyme EcoRI and then, from this digest, the EcoRI fragment approximately 5 kb in size containing the *Aspergillus foetidus* SE4 glucoamylase promoter, coding region and terminator is isolated according to the method described by ZHU et al., 1985.

This EcoRI fragment is then inserted into plasmid pUC18 which has previously been digested with the restriction enzyme EcoRI. The vector pFGA2 (FIG. 3) is thereby created.

The nucleotide sequences of the *Aspergillus foetidus* SE4 glucoamylase promoter and terminator were determined by the dideoxynucleotide chain termination method of SANGER et al. (1977) Proc. Natl. Acad. Sci. USA 74, pages 5463–5467.

Analysis of this sequence shows the presence of a promoter and a terminator. The nucleotide sequence (SEQ ID NO:7) coding for the *Aspergillus foetidus* SE4 glucoamylase promoter is identified. The nucleotide sequence (SEQ ID NO:8) coding for the *Aspergillus foetidus* SE4 glucoamylase terminator is identified.

FIG. 6 shows the nucleotide sequence coding for the *Aspergillus foetidus* SE4 glucoamylase promoter.

FIG. 7 shows the nucleotide sequence coding for the *Aspergillus foetidus* SE4 glucoamylase terminator.

The synthetic oligonucleotides used to initiate elongation reactions with T7 DNA polymerase were synthesized by the method of BEAUCAGE et al. (1981) Tetrahedron letters 22, pages 1859–1882. Sequencing was performed according to the protocol given by the supplier of the sequencing kit (PHARMACIA), performing a denaturation of the double-stranded DNA by treatment with NaOH.

The sequencing strategy is described by SAMBROOK, 1989, pages 13.15 and 13.17. Polyacrylamide sequencing gels were prepared according to the technique described by SAMBROOK, 1989, pages 13.45–13.58.

A plasmid which is derived from plasmid pFGA2, and which contains the *Aspergillus foetidus* SE4 glucoamylase gene in which the promoter and the terminator are separated from the coding portion by NotI and HindIII restriction sites, is constructed as described below. Two restriction sites, NotI and HindIII, are thereby created in plasmid pFGA2, which contains the promoter and the terminator. The *Aspergillus*

*foetidus* SE4 glucoamylase promoter and terminator are separated by NotI and HindIII restriction sites created by two directed mutageneses according to the procedure described in the technical leaflet of the mutagenesis kit (BIORAD) "MUTA-GENE PHAGEMID in vitro Mutagenesis Kit".

The synthetic oligonucleotides used during this procedure are the following, SEQ ID NO:5 and SEQ ID NO:6, respectively:

5' - GCCTGAGCTTCATCCCCAGCGCGGCCGCATCATTACACCTCAGCAATGT - 3'
                              NotI

5' - TGACTGACACCTGGCGGTGAAAGCTTCAATCAATCCATTTCGCTATAGTT - 3'
                              HindIII The vector pFGA2MUT, which contains the NotI restriction site at the beginning of the untranslated 5' region of the glucoamylase gene and the HindIII cleavage site after the stop codon and in the untranslated 3' region of glucoamylase, is thereby obtained.

EXAMPLE 3
Construction of the integration vector

Following the digestion of plasmid pUCGOD, obtained as described in Example 1, with the two restriction enzymes NotI and HindIII, a fragment containing the glucose oxidase coding sequence and the untranslated 5' region of the *Aspergillus foetidus* SE4 glucoamylase gene is isolated according to the technique described by ZHU, J. D. et al., BIO/TECHNOLOGY, 3, 1985, pages 1014–1016.

Partial and complete digestion of the plasmids with restriction enzymes is performed according to the technique described by SAMBROOK et al., 1989, Chapters 5.28–5.32.

This fragment is introduced into the NotI-HindIII cloning site of plasmid pFGA2MUT, obtained as described in Example 2. This plasmid contains the promoter and terminator of the *Aspergillus foetidus* SE4 glucoamylase gene separated by NotI and HindIII cloning sites created by directed mutagenesis. The glucoamylase coding portion is hence replaced by the glucose oxidase coding portion.

The vector pFGOD (FIG. 5) is thereby obtained. This vector PFGOD contains the glucose oxidase coding sequence, which comprises its own secretion signal, under the control of the *Aspergillus foetidus* glucoamylase transcription signals. This vector contains the expression system which comprises the following sequences:

- the *Aspergillus foetidus* SE4 glucoamylase promoter sequence,
- the *Aspergillus foetidus* ATCC 14916 glucose oxidase secretion signal sequence,
- the mature sequence of *Aspergillus foetidus* ATCC 14916 glucose oxidase, and
- the *Aspergillus foetidus* SE4 glucoamylase terminator sequence.

EXAMPLE 4
Transformation of *Aspergillus foetidus* strain SE4

*Aspergillus foetidus* strain SE4 is derived from *Aspergillus foetidus* strain ATCC 14916.

*Aspergillus foetidus* strain ATCC 14916 is first subjected to a mutagenesis treatment with ultraviolet according to the technique described in PONTECORVO, G., ROPER, J. A., HEMMONS, L. M., MACDONALD, K. D., and BUFTON, A. W. J., Advances in Genetics 5 (1953), pages 141–238.

The treated strains are plated out on an agar nutrient medium POTATO DEXTROSE AGAR (DIFCO) to which starch (5% weight/volume) has been added. After incubation for 48 hours at 32° C., the colonies displaying the largest halo of hydrolysis of starch are removed and subcultured on the agar nutrient medium. A strain producing a large amount of glucoamylase is isolated. This strain, designated SE4, possesses pale brown conidia.

The vector pFGOD is then introduced into *Aspergillus foetidus* strain SE4 by cotransformation according to the technique described in CARREZ et al., GENE, 94 (1990), pages 147–154.

Plasmid p3SR2, which contains the *Aspergillus nidulans* acetamidase gene (amdS), is used as a selective marker.

Plasmid p3SR2 is described in Hynes, M. J., Corrick, C. M., and King, J. A., Mol. Cell. Biol., 3 (1983), pages 1430–1439. Transformation is performed with this plasmid according to the technique described by KELLY, J. M. and HYNES, M. J., EMBO J. 4 (1985), pages 475–479.

*Aspergillus foetidus* strain SE4 was transformed with equimolar amounts of plasmids p3SR2 and pFGOD.

Approximately 350 transformed strains are obtained. These transformed strains are selected on agar medium A containing ABTS (BOEHRINGER) to detect the production of glucose oxidase. Colonies of the transformed strains which also secrete glucose oxidase into the culture medium are surrounded by a green halo after 2 hours of incubation at 32° C.

Medium A is composed of CZAPEK DOX AGAR medium (DIFCO) to which 10% (weight/volume) of glucose, 0.05% (weight/volume) of ABTS (2,2'-azinobis(3-ethylbenzthiazolinesulphonate)) (BOEHRINGER) and 8 mg/l of horse-radish peroxidase (46 purpurogallin units/mg, SIGMA) are added.

Approximately 40% of the transformed strains secrete glucose oxidase; hence they have integrated the selectable vector p3SR2 and the integration vector pFGOD in their genome.

EXAMPLE 5
Isolation and purification of transformed strains

The transformed strains displaying the largest halo are isolated and subcultured on an agar medium POTATO DEXTROSE AGAR (DIFCO). 50 transformed strains are cultured at 32° C. on this medium until sporulation takes place.

The spores are harvested, diluted in physiological solution and then plated out on agar medium A in such a way that individual colonies are obtained. Colonies coming from a single spore and displaying a broad halo are subcultured on the agar medium POTATO DEXTROSE AGAR. These colonies are cultured at 32° C. on this agar medium until sporulation takes place.

The purified conidia of the transformed strains are harvested and stored. These transformed strains of *Aspergillus foetidus* are designated SE4tr.

EXAMPLE 6
Production of glucose oxidase by the transformed strain *Aspergillus foetidus* SE4tr The purified conidia obtained in Example 5 are cultured in a rich liquid medium containing malt extract (DIFCO)

(2% by weight), peptone (DIFCO) (0.1% by weight), hydrolysed starch (10% by weight) and calcium carbonate (3.5% by weight). The pH of the culture medium is adjusted to pH 6 by adding ammonia. Culturing is carried out at 32° C. with agitation and is monitored for 5 days.

The culture obtained is then centrifuged at 5,000 rpm for 15 minutes (BECKMAN JA-10). The enzymatic (glucose oxidase) activity is measured on the biomass, after the cells have been disrupted and dismembered by grinding the biomass which has been frozen with liquid nitrogen (so-called intracellular production), and on the supernatant (so-called extracellular production), according to the technique described in FIEDUREK, J., et al., Enzyme Microb. Technol. 8 (1986), pages 734–736.

The results for enzymatic activity obtained are compared with those of the untransformed strain of *Aspergillus foetidus* (strain SE4). The intracellular glucose oxidase production of the transformed strain (strain SE4tr) in comparison with that of the untransformed strain (strain SE4) is multiplied by a factor of 5 to 10, and the extracellular production is multiplied by a factor of 5000 to 10,000.

A large increase in extracellular glucose oxidase production is observed. In effect, the transformed strain secretes almost all of the glucose oxidase it produces into the culture medium. The glucose oxidase produced by the untransformed strain is hardly secreted into the culture medium. A step of disruption of the cells of the untransformed strain is thus essential in order to recover the glucose oxidase, which is no longer necessary with the transformed strain according to the invention. Glucose oxidase production by the transformed strain SE4tr is substantially extracellular.

Moreover, catalase is hardly detected in the supernatant of the fermentation medium obtained after culturing the transformed strain SE4tr.

EXAMPLE 7

Profile of activity as a function of pH for the glucose oxidase produced by the transformed strain SE4tr The enzymatic activity of the glucose oxidase is measured at different pH values (from 3.5 to 9.0) at a temperature of 25° C. in a buffer. The conditions applied are those described in Example 6.

The supernatant obtained in Example 6 is employed. This supernatant is diluted in accordance with the pH and the enzymatic activity in distilled water, and then in 0.1M citrate/phosphate buffer for the pH range 3.5 to 5.5 and in 0.1M $KH_2PO_4/K_2HPO_4$ buffer for the pH range 6.0 to 9.0.

2.5 ml of an aqueous solution of substrate are added to 50 microliters of diluted supernatant at 25° C. The aqueous solution of substrate contains 10% (weight/volume) of glucose, 0.05% (weight/volume) of ABTS and 12 mg/l of horseradish peroxidase. The pH of the aqueous solution of substrate is adjusted with 0.1M citrate/phosphate buffer for the pH range 3.5 to 5.5 or with 0.1M $KH_2PO_4/K_2HPO_4$ buffer for the pH range 6.0 to 9.0.

The absorbence is measured at 420 nm after incubation for 2 minutes.

The results are collated in Table 2.

During this test, the maximum enzymatic activity was measured for the sample placed at a pH of approximately 5.5 and at a temperature of 25° C. By definition, this sample was hence assigned a relative activity of 100%.

This example shows that glucose oxidase displays optimal enzymatic activity, measured at a temperature of approximately 25° C., in a pH range between approximately 4.0 and approximately 7.0.

TABLE 2

| | Relative activity in % Glucose oxidase produced by the | |
|---|---|---|
| pH | untransformed strain | transformed strain |
| 3.5 | 47 | 43 |
| 4.0 | 69 | 66 |
| 5.0 | 98 | 99 |
| 5.5 | 100 | 100 |
| 6.0 | 98 | 98 |
| 6.5 | 88 | 86 |
| 7.0 | 67 | 63 |
| 8.0 | 34 | 30 |
| 8.5 | 14 | 14 |
| 9.0 | 9 | 8 |

The profile of activity as a function of pH of the glucose oxidase produced by the transformed strain is similar to that of the glucose oxidase produced by the untransformed strain, that is to say the native enzyme.

EXAMPLE 8

Profile of activity as a function of temperature for the glucose oxidase produced by the transformed strain SE4tr The enzymatic activity of the glucose oxidase is measured at different temperatures (from 20° to 50° C.) at a pH of 6.0 in 0.1M $KH_2PO_4/K_2HPO_4$ buffer. The conditions applied are those described in Example 6.

The supernatant as obtained in Example 6 is employed. This supernatant is diluted in accordance with the pH and the enzymatic activity in distilled water, and then in 0.1M $KH_2PO_4/K_2HPO_4$ buffer.

2.5 ml of an aqueous solution of substrate are added to 50 microliters of diluted supernatant. The aqueous solution of substrate contains 10% (weight/volume) of glucose, 0.05% (weight/volume) of ABTS and 12 mg/l of horseradish peroxidase. The pH of the aqueous solution of substrate is adjusted to a pH of 6.0 with 0.1M $KH_2PO_4/K_2HPO_4$ buffer. Before being mixed, the aqueous solution of substrate and the diluted supernatant are heated to the desired temperature.

The absorbence is measured at 420 nm after incubation for two minutes.

The results are collated in Table 3.

During this test, the maximum enzymatic activity was measured for the sample placed at a pH of approximately 6.0 and at a temperature of 35° C. By definition, this sample was hence assigned a relative activity of 100%.

This example shows that glucose oxidase displays optimal enzymatic activity, measured at a pH of approximately 6.0, in a temperature range between approximately 20 and approximately 50° C.

TABLE 3

| | Relative activity in % glucose oxidase produced by the | |
|---|---|---|
| temperature °C. | untransformed strain | transformed strain |
| 20 | 79 | 82 |
| 30 | 99 | 99 |
| 35 | 100 | 100 |
| 40 | 99 | 97 |
| 50 | 83 | 76 |

The profile of activity as a function of temperature of the glucose oxidase produced by the transformed strain is similar to that of the glucose oxidase produced by the untransformed strain, that is to say the native enzyme.

Examples 7 and 8 show that the features of the glucose oxidase produced by the transformed strain are similar to those of the glucose oxidase produced by the untransformed strain.

---

We claim:

1. An expression system comprising:

a promoter, a glucose oxidase secretion signal sequence, a gene encoding mature glucose oxidase, and a terminator;

wherein said promoter, signal sequence, gene and terminator are each derived from a filamentous fungus.

2. The expression system of claim 1, wherein said filamentous fungus is an Aspergillus strain.

3. The expression system of claim 2, wherein said Aspergillus strain is an *Aspergillus foetidus* strain.

4. The expression system of claim 3, wherein said *Aspergillus foetidus* strain produces more glucoamylase than is produced by *Aspergillus foetidus* strain ATCC 14916 under equivalent conditions.

5. The expression system of claim 1, wherein said terminator is a glucoamylase terminator.

6. The expression system of claim 5, wherein said glucoamylase terminator has the nucleotide sequence of SEQ ID NO:8.

7. The expression system of claim 5, wherein said glucoamylase terminator sequence is obtained from a strain of *Aspergillus foetidus*.

8. The expression system of claim 7, wherein said strain of *Aspergillus foetidus* produces more glucoamylase than is produced by *Aspergillus foetidus* strain ATCC 14916 under equivalent conditions.

9. The expression system of claim 1, wherein said glucose oxidase secretion signal sequence is obtained from *Aspergillus foetidus* strain ATCC 14916.

10. The expression system of claim 1, wherein said DNA encoding said mature glucose oxidase is obtained from *Aspergillus foetidus* strain ATCC 14916.

11. An integration vector containing the expression system of claim 1.

12. The integration vector of claim 11, which is a plasmid.

13. The integration vector of claim 12 which is the plasmid PFGOD.

14. A cell transformed by the plasmid of claim 13.

15. A cell transformed by the integration vector of claim 11.

16. The transformed cell of claim 15 which is a filamentous fungus.

17. The transformed cell of claim 16, wherein said filamentous fungus is an Aspergillus.

18. The transformed cell of claim 17, wherein said Aspergillus is *Aspergillus foetidus*.

19. A process for producing glucose oxidase extracellularly, comprising the steps of:

transforming a host cell with an integration vector containing the expression system of claim 1, culturing the transformed cell in culture medium, and recovering glucose oxidase from the culture medium.

20. The expression system of claim 1, wherein said promoter sequence is a glucoamylase promoter.

21. The expression system of claim 20, wherein said glucoamylase promoter sequence is obtained from a strain of *Aspergillus foetidus*.

22. The expression system of claim 21, wherein said strain of *Aspergillus foetidus* produces more glucoamylase than is produced by *Aspergillus foetidus* strain ATCC 14916 under equivalent conditions.

23. The expression system of claim 21, wherein said glucoamylase promoter has the nucleotide sequence of SEQ ID NO:7.

24. The isolated and purified *Aspergillus foetidus* strain SE4tr.

25. The isolated *Aspergillus foetidus* glucoamylase promoter.

26. The promoter of claim 25 which has the nucleotide sequence of SEQ ID NO:7.

27. The isolated *Aspergillus foetidus* glucoamylase terminator.

28. The terminator of claim 27 which has the nucleotide sequence SEQ ID NO:8.

\* \* \* \* \*